(12) United States Patent
Crainich

(10) Patent No.: US 6,226,843 B1
(45) Date of Patent: May 8, 2001

(54) LIGATING CLIP

(75) Inventor: Lawrence Crainich, Charlestown, NH (US)

(73) Assignee: Design Standards Corporation, Charlestown, NH (US)

( * ) Notice: Subject to any disclaimer, the term of this patent is extended or adjusted under 35 U.S.C. 154(b) by 0 days.

(21) Appl. No.: 09/257,891

(22) Filed: Feb. 25, 1999

(51) Int. Cl.⁷ .............................. A44B 21/00; B42F 1/00
(52) U.S. Cl. .............................. 24/545; 24/67.9; 24/546; 24/555; 24/563
(58) Field of Search .................. 24/545, 546, 547, 24/552, 555, 563, 67.9; 606/158

(56) References Cited

U.S. PATENT DOCUMENTS

| | | | |
|---|---|---|---|
| 866,141 | * | 9/1907 | Kay, Jr. .................................. 24/547 |
| 1,417,850 | * | 5/1922 | Marshall ................................ 24/555 |
| 1,546,198 | * | 7/1925 | Brummitt ............................... 24/67.9 |
| 2,134,849 | * | 11/1938 | Arnold .................................... 24/546 |
| 2,711,637 | * | 6/1955 | Wells ..................................... 24/555 |
| 3,827,438 | * | 8/1974 | Kees, Jr. ................................ 24/545 |
| 3,996,937 | * | 12/1976 | Williams ................................ 24/546 |
| 4,024,868 | * | 5/1977 | Williams ............................... 128/325 |
| 4,660,558 | * | 4/1987 | Kees, Jr. ................................ 24/546 |
| 4,738,007 | * | 4/1988 | Demarest, Jr. ......................... 24/563 |
| 4,765,335 | * | 8/1988 | Schmidt et al. ....................... 24/545 |
| 4,943,298 | * | 7/1990 | Fujita et al. .......................... 606/158 |
| 5,312,426 | * | 5/1994 | Segawa et al. ....................... 606/158 |
| 5,593,414 | | 1/1997 | Shipp et al. . |

FOREIGN PATENT DOCUMENTS

189814 * 10/1907 (DE) ..................................... 24/546

* cited by examiner

*Primary Examiner*—Victor N. Sakran
(74) *Attorney, Agent, or Firm*—Bachman & LaPointe, P.C.

(57) ABSTRACT

A ligating clip includes a substantially planar head portion and at least two legs each extending away from the head portion. The head portion is resilient and spring biased toward a closed position, and the legs can be positioned in a plane defining an angle with the planar head portion of greater than about 90° and less than about 180°, which provides for better visibility of clips during application of the clip.

26 Claims, 4 Drawing Sheets

LIGATING CLIP

BACKGROUND OF THE INVENTION

The invention relates to a ligating clip which is useful for various surgical procedures, particularly for clamping around tissues such as vessels, ducts and the like.

Ligating or ligation clips are well known in the surgical field for use in clamping and thereby ligating various vessels and ducts. This is done so as to control bleeding during surgical procedures.

A large number of disclosures and efforts have been made so to provide satisfactory ligating clips. Despite these efforts, continued problems remain in connection with the provision of ligating clips which are simple and reliable in use, which are easily positioned for proper application, which provide sufficient and reliable closing or ligating of tissues during use, and which can also be removed in a simple procedure.

It is therefore the primary object of the present invention to provide a ligating clip which is easily positioned for use in ligating desired tissues.

It is a further object of the present invention to provide a ligating clip which provides secure clamping of tissues so as to close and reliably stop bleeding of a particular vessel to which the clip is applied.

It is a still further object of the present invention to provide a ligating clip as above which is readily removed from tissues if desired.

Other objects and advantages of the present invention will appear hereinbelow.

SUMMARY OF THE INVENTION

In accordance with the present invention, the foregoing objects and advantages have been readily attained. According to the invention, a ligating clip is provided which comprises a substantially planar head portion; and at least two legs each extending away from said head portion, said head portion biasing said legs into a closed position and being resiliently flexible to allow said legs to be spread to an open position, said head portion having sides extending wider than said legs whereby said sides are engagable for positioning said clip.

The ligating clip of the present invention may be provided including a tissue stop segment for advantageously preventing tissue from passing into a loop of the head portion.

One or both legs of the ligating clip of the present invention can be provided having a plurality of spaced leg segments defining spaces therebetween. The leg segments of respective legs can also be positioned relative to the other legs so as to position opposing legs aligned with spaces. This advantageously allows for occlusion of tissues clamped between the legs of the clip device through compression and diversion or displacement.

The clip of the present invention can be made of resilient elastic wire formed so as to be biased to a closed position, so that legs of the clip can be tensioned to an open position, released to a clamped position, and again tensioned for removal if desired.

BRIEF DESCRIPTION THE DRAWINGS

A detailed description of preferred embodiments of the present invention follows, with reference to the attached drawings, wherein.

Figure 5:
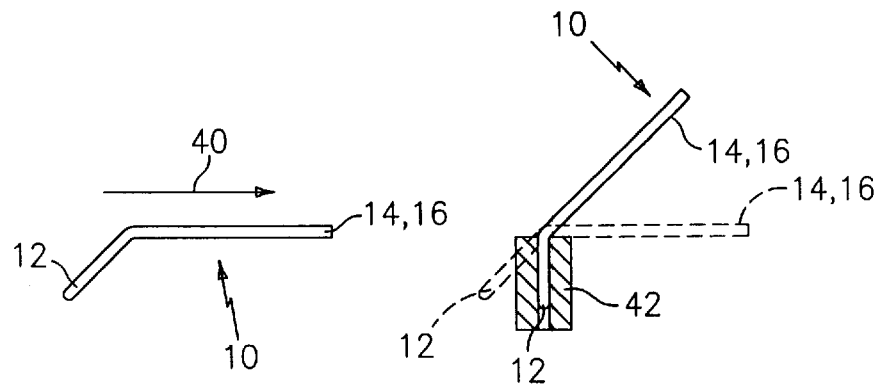
Figure 6:
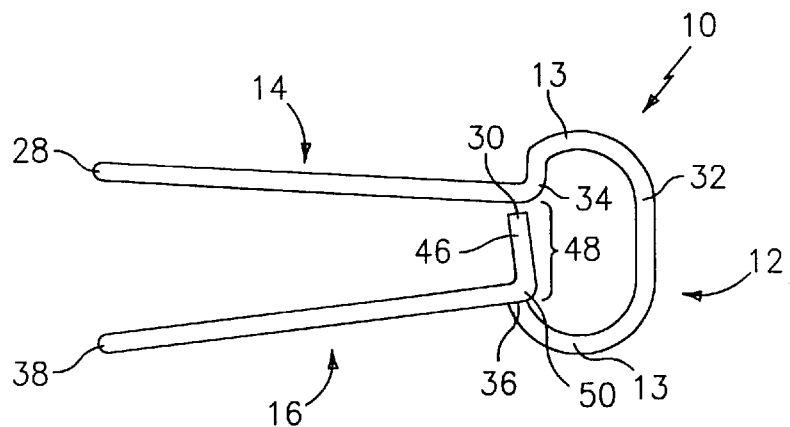
Figure 7:
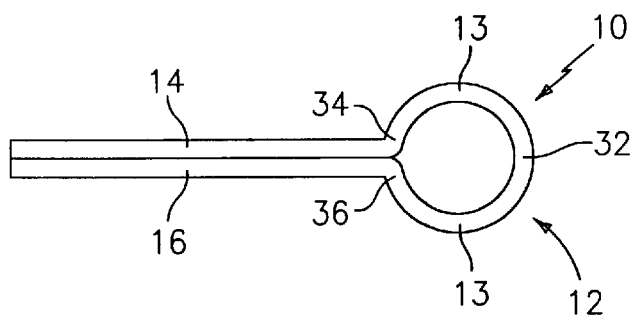
Figure 14:
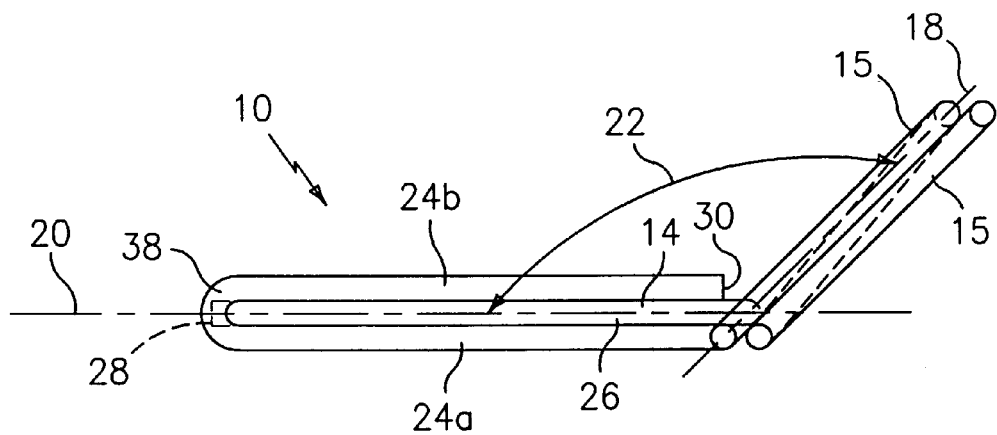

FIG. 5 schematically illustrates the advantageous use of clips in accordance with the present invention;

FIG. 6 illustrates an alternative embodiment of the clip of the prevent invention in an open position;

FIG. 7 illustrates a further alternative embodiment of the present invention;

FIGS. 8–13 illustrate various types of ligation which can be accomplished using conventional ligating clips and using ligating clips in accordance with the present invention;

FIG. 14 illustrates a multiple coil embodiment of the present invention; and

Figure 15:
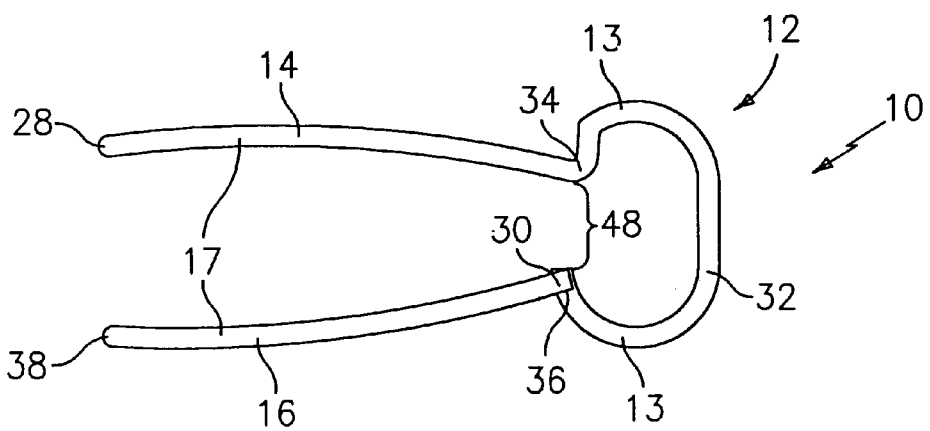

FIG. 15 illustrates an embodiment of the invention having pre-stressed arcuate legs.

DETAILED DESCRIPTION

The invention relates to a ligating clip having advantageous features which allow for ease in positioning during use, reliable occlusion and ligation of tissues to be clamped within the clip, prevention of escape of tissue from between the clamping legs of the clip, and efficient onepiece construction.

Figure 1:
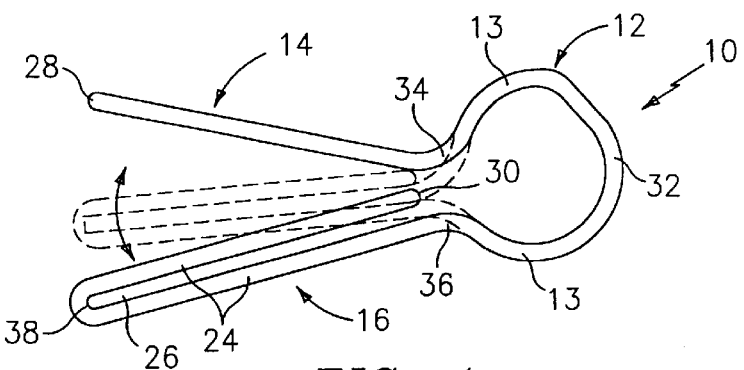
FIG. 1 is a perspective view of a ligating clip according to the present invention deflected to an open position and illustrated by dashed lines in a closed position.

FIG. 1 shows a perspective view of a preferred embodiment of clip 10 in accordance with the present invention. As shown, clip 10 includes a head portion 12 which is preferably formed as a loop or ring of wire material, a first leg 14 extending from head portion 12, and a second leg 16 extending from head portion 12.

According to the invention, at least head portion 12 is formed of a resilient and elastic material having a rest position which positions first leg 14 and second leg 16 in a substantially adjacent and/or contacting closed position as shown in dashed lines in FIG. 1. Further, the resilient and elastic nature of head portion 12 allows for legs 14, 16 to be deflected or tensioned to an open position as shown in solid lines in FIG. 1 to allow tissues such as vessels, ducts and the like to be positioned therebetween for clamping as desired. Head portion 12 is preferably configured so as to be opened, to a larger circumference, through opening of legs 14, 16.

Figure 2:
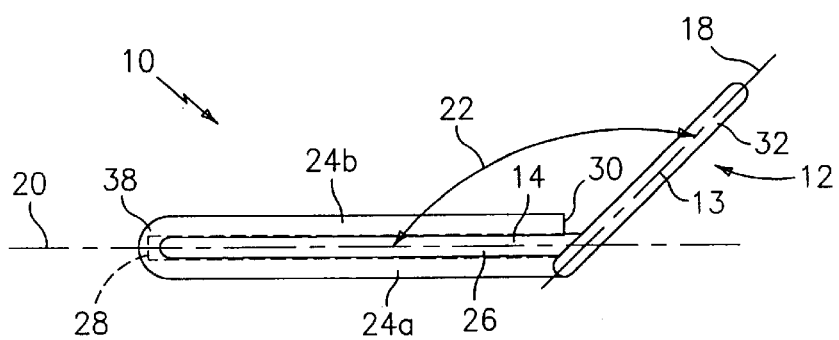
FIG. 2 is a side view of a clip in accordance with the present invention.
Figure 3:
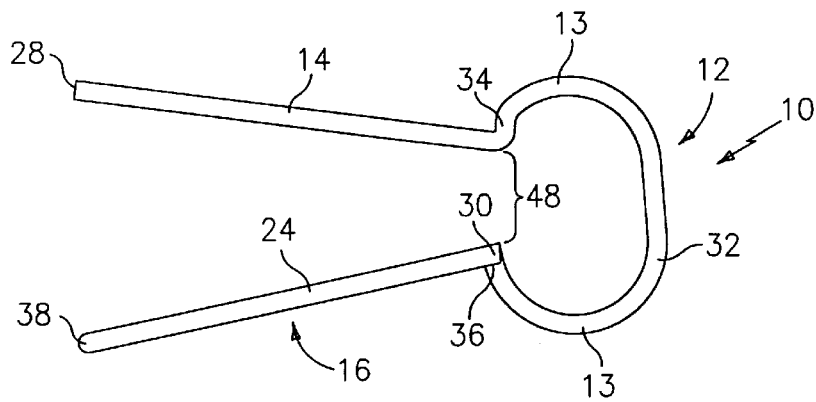
FIG. 3 is a top view of a clip in accordance with the present invention in an open position.
Figure 4:
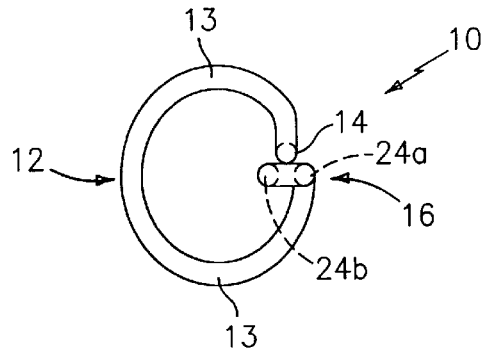
FIG. 4 is an end view of a clip according to the present invention in a closed position.

FIG. 2 shows a side view of clip 10 in accordance with the present invention, and highlights an advantage of the clip of the present invention. As shown, head portion 12 is preferably substantially planar in shape, and falls in a plane 18. Head portion 12 preferably has side portions 13 which extend beyond a width of legs 14, 16 in the closed position. This advantageously allows for engaging head portion 12 through sides 13 so as to position or orient clip 10 in a desired position or orientation for use.

In addition, legs 14, 16 preferably extend from head portion 12 in a plane 20. According to the invention, and advantageously, head portion 12 and legs 14, 16 are preferably formed so that planes 18, 20 define an angle 22 therebetween which is greater than 90° and less than 180°. This is advantageous in that, as will be discussed further below, head portion 12 can be easily manipulated in an applicator having perpendicular or vertical surfaces or grooves for positioning clips so as to position head portion 12 substantially vertical, and thereby extend legs 14, 16 from the applicator at an angle to improve visibility of legs 14, 16 during application to tissue during a surgical procedure such as laparascopic surgery.

It is preferred that head portion 12 and legs 14, 16 be positioned so as to define planes 18, 20 at angle 22 of between about 105° and 165°, and most preferably between about 120°and about 150°.

Referring back to FIG. 1, at least one leg 16 may be provided having a plurality, in this case two, leg segments 24. Leg segments 24 are advantageously provided by forming the wire of clip 10 back upon itself. Leg segments 24 define a space 26 therebetween, and the opposing leg 14 may be aligned with space 26. As will be further illustrated in FIGS. 9–13 below, multiple leg segments advantageously provide for closing off of blood vessels, ducts and the like, and aligning segments with spaces can also provide diversion or displacement, as well as compression, so as to provide reliable grip of the clip on the intended tissue, and improved closure of same.

Clip 10 may suitably be provided or formed from a suitable wire material, for example wrought titanium alloy wire, although a wide variety of other materials could be used, such as for example, implantable stainless steel, memory metal and the like. The wire may be provided of substantially circular, square or rectangular cross section, or in combinations, or may be of any other cross section which facilitates appropriate use thereof. In addition, tissue contacting portions of legs 14, 16 may suitably be flattened and/or textured to provide better grip of tissue.

Clip 10 can advantageously be manufactured from a single strand or length of such wire. The clip shown in FIGS. 1–4 is formed from a piece of wire having a first wire end 28 and a second wire end 30. The wire of clip 10 defines a loop portion 32 as head portion 12 having sides 13. Loop portion 32 falls substantially in plane 18 as described above, and the loop terminates in loop ends 34, 36. First leg 14 extends from loop end 34 at the desired angle 22, and terminates in first wire end 28 as shown. Second leg 16 extends from loop end 36, also at angle 22. Second leg 16 includes two leg segment 24a, 24b and a substantially U-shaped bend 38 connecting segments 24a, 24b and defining a distal end of leg 16. Segment 24b of second leg 16 terminates in second wire end 30 substantially adjacent to loop portion 32.

As shown, leg segments 24a, 24b define space 26 therebetween, and space 26 in this embodiment is aligned as desired with first leg 14 so as to provide the desired occlusion of tissues therebetween.

As set forth above, the angling of head portion 12 relative to legs 14, 16 in accordance with the present invention advantageously provides for ease of positioning of clip 10 during use. Referring to FIG. 5, typical movement of a clip 10 within a clip applicator is illustrated by arrow 40. A suitable applicator will be provided with structure 42 preferably defining a substantially vertical or perpendicular "V" groove at an outlet portion of the applicator. For example, the applicator may have jaws each having structure 42 defining a groove. When the jaws engage a clip, and the clip reaches the outlet end of the applicator and can pivot, sides 13 of head portion 12 are guided into the groove and head portion 12 is positioned substantially vertically, thereby pivoting first and second legs 14, 16 to an angle with respect to the longitudinal direction of movement 40 of clips 10, or direction of extent of the applicator tool, so as to position legs 14, 16 in an easily visible location to facilitate proper positioning around a desired tissue. Thus, the forming of head portion 12 relative to legs 14, 16 so as to define angle 22 as desired provides for excellent visibility of clip 10 during application which is especially useful during laparascopic surgery. This is, particularly true for the specific preferred angles, since the provision of a structure 42 defining a vertical groove is a very simple and stable configuration of an applicator.

FIG. 6 illustrates an alternative embodiment of the present invention wherein second leg 16 has leg segments 24a, 24b,(as shown in FIG. 2) and wherein second leg 16 further includes a tissue stop segment 46 which extends from leg segment 24b so as to close a gap 48 (also shown in FIG. 2) which is formed between loop ends 34, 36 when clip 10 is in the open position as shown. Tissue stop segment 46 preferably extends from an end 50 of leg segment 24b, preferably substantially perpendicular to leg segment 24b, from a position which is preferably substantially adjacent to loop portion 32, and in a direction toward first leg 14 as shown in FIG. 6. This positioning of tissue stop 46 advantageously serves to prevent tissue from slipping into the interior portion of loop 32 or head portion 12, thereby insuring that tissue to be grasped or clamped within clip 10 will be entirely positioned between legs 14, 16, and no portion of such tissue will be allowed to pass into the interior of head portion 12 and thereby avoid clamping. In this embodiment, tissue stop 46 terminates in second wire end 30, although other configurations are possible within the scope of the present invention.

FIG. 7 illustrates a still further alternative embodiment of the present invention wherein head portion 12 and legs 14, 16 are angled relative to each other as desired and illustrated, for example in FIG. 2. However, in this embodiment, first and second legs 14, 16 are each a single wire leg segment, and each leg terminates in a distal first and second wire end 28, 30. In this embodiment, ligation of a particular tissue would be accomplished through conventional surface to surface clamping as illustrated in FIG. 8, but the advantageous positioning allowed by angling of head portion 12 relative to first and second legs 14, 16 would nevertheless be present.

It should be noted that first leg 14 of clip 10 could advantageously be provided having multiple leg segments 24, in similar fashion to second leg 16 of the embodiment of FIGS. 1–4. This could be accomplished by bending leg 14 back on itself in the same matter as leg 16. Further, if desired, either or both legs 14, 16 could be configured to have three or more parallel segments 24 either in the same plane, or in a non-planar arrangement (see FIGS. 12 and 13). The foregoing embodiments would provide a plurality of leg segments on each leg 14, 16, with each pair defining spaces therebetween. In this configuration, at least one leg segment of leg 14 is positioned aligned with a space 26 of leg 16 so as to provide for one or more displacements of tissue between legs 14, 16 to occlude tissue as desired.

Figure 8:
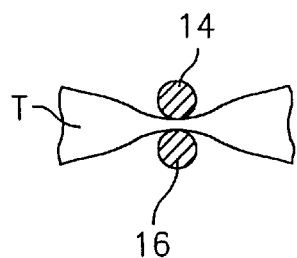
Figure 9:
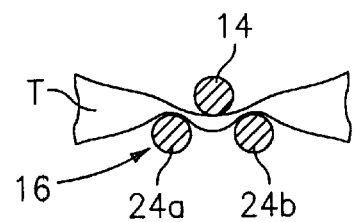
Figure 10:
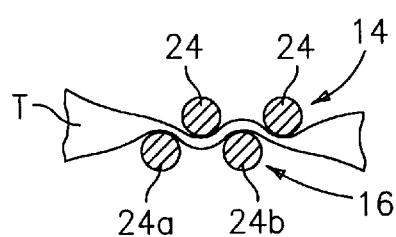

FIGS. 8–10 illustrate the clamping obtained using conventional leg to leg contact on a tissue T (FIG. 8), the occlusion advantageously obtained using a single first leg 14 and a second leg 16 having leg segments 24a, 24b (FIG. 9), and the further advantageous occlusion obtained according to the invention using multiple leg segments 24 for both first leg 14 and second leg 16 (FIG. 10).

Figure 11:
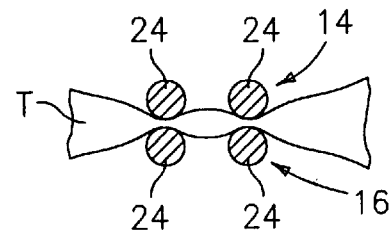

FIG. 11 shows a multiple leg segment 24 embodiment wherein segments 24 of legs 14, 16 are aligned together.

Figure 12:
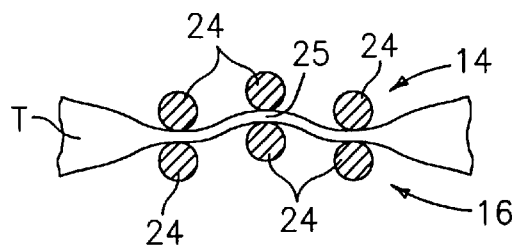

FIG. 12 shows an embodiment wherein legs 14, 16 each have three (3) segments 24, which are parallel but nonplanar. This advantageously provides displacement of a portion 25 of tissue T as shown.

Figure 13:
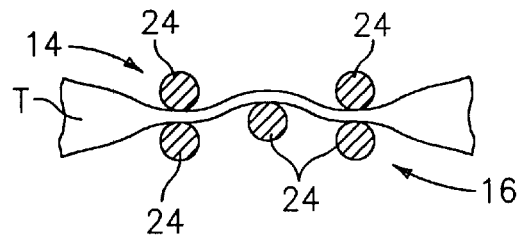

FIG. 13 shows an embodiment having a two segment 24 leg 14 and a three (3) segment 24 non-planar leg 16.

In accordance with the present invention, clip 10 can be positioned as desired in accordance with the following procedure.

Clips 10 are initially preferably provided in a serial arrangement for repeated application from an applicator device. Clips are advanced toward an applicator head, and picked off from following clips by jaws or other structure for positioning in an application position, for example as schematically illustrated in FIG. 5. Head portion 12 of clip 10 is then located or guided into the V groove defined by structure 42 of the applicator, thereby advantageously pivoting or canting legs 14, 16 into an easily visible position. At some point along this process, or in the pivoted and ready position illustrated in FIG. 5, legs 14, 16 are then deflected into an open position, for example through application of a spreading force to the interior surfaces of head portion 12. This may be accomplished by spreading structure 42 while engaged with clip 10. This advantageously serves to spread legs 14, 16 to allow positioning of clip 10 around tissue as desired. Such positioning can be performed with a large degree of precision and certainty due to the visibility of legs 14, 16 provided by the specific features of the invention. Release of legs 14, 16, for example through removal of application of the spreading force to the inner surfaces of head portion 12, allows legs 14, 16 to close back to the rest or "biased toward" position, thereby advantageously clamping tissue between legs 14, 16 in a secure position. Further, tissue stop 46 advantageously blocks tissue from entering head portion 12 during positioning, thereby ensuring that all desired tissue is clamped.

When it is desired to remove clip 10, such removal can be facilitated through again applying a spreading force to inner surfaces of sides 13 of head portion 12 so as to spread legs 14, 16, thereby releasing tissue from clip 10 and releasing clip 10 for ease in removal from the application site, or for repositioning clip 10 in a different location or angular orientation.

FIG. 14 illustrates an alternative embodiment of the invention wherein head portion 12 has multiple loops 15 as opposed to the single loop of the embodiments of FIGS. 1–7. Clip 10 of this embodiment is in all other respects the same as described above. A plurality of loops 15 helps by providing additional flexible material which advantageously allows legs 14, 16 to be spread further without damaging clip 10. FIG. 14 shows two loops 15, although more than two loops could be used if desired.

Referring to FIG. 15, another alternative embodiment is provided wherein clip 10 has legs 14, 16 which are pre-stressed or otherwise formed so as to be biased toward an arcuate shape in the open position as shown. The arcuate shape of legs 14, 16 defines concave portions or sides 17 of legs 14, 16 which are positioned facing each other, and legs 14, 16 are flexible so that they are deflected toward a straight shape in the closed position as illustrated in the embodiments of FIGS. 1–7. During closing, legs 14, 16 of the embodiment of FIG. 15 close first at the tips and then flex for parallel closure. This is desirable so as to provide a uniform tissue clamping force which can help to avoid tissue necrosis. This embodiment could be used in connection with any of the above-mentioned configurations including single legs 14, 16, or multiple leg segments 24, or both.

It should readily be appreciated that a ligating clip has been provided in accordance with the present invention which advantageously solves a number of problems experienced by the industry, and which readily accomplishes each and every objective set forth above. The ligating clip provided in accordance with the present invention is easy to use, reliable in use, and efficient in manufacture.

It is to be understood that the invention is not limited to the illustrations described and shown herein, which are deemed to be merely illustrative of the best modes of carrying out the invention, and which are susceptible to modification of form, size, arrangement of parts and details of operation. The invention rather is intended to encompass all such modifications which are within its spirit and scope as defined by the claims.

What is claimed is:

1. A ligating clip, comprising:
a substantially planar head portion; and
at least two legs each extending away from said head portion, said head portion biasing said legs into a closed position and being resiliently flexible to allow said legs to be spread to an open position, wherein said at least two legs each extend away from said head portion in a plane defining an angle with said planar head portion of greater than 90° and less than 180°, and wherein said head portion has sides extending wider than said legs whereby said sides are engagable for positioning and opening said clip.

2. A clip according to claim 1, wherein said angle is between about 105° and about 165°.

3. A clip according to claim 1, wherein said angle is between about 120° and about 150°.

4. A clip according to claim 3, wherein said loop encompasses a larger area in said open position than in said closed position.

5. A clip according to claim 1, wherein said head portion is a resilient wire formed into a loop defining said sides and having two loop ends, and wherein said at least two legs extend from said two loop ends.

6. A clip according to claim 5, wherein said angle is defined at a point where said two legs meet said two loop ends.

7. A clip according to claim 1, wherein said at least two legs are deflectable in a plane of motion between said open position wherein said legs are spaced from each other and said closed position wherein said legs are substantially adjacent to each other.

8. A clip according to claim 7, wherein at least one of said at least two legs comprises a plurality of parallel leg segments spaced from each other in a plane substantially perpendicular to said plane of motion.

9. A clip according to claim 8, wherein said leg segments define a space therebetween, and wherein the other of said at least two legs is aligned with said space.

10. A clip according to claim 1, wherein at least one of said at least two legs comprises a plurality of parallel leg segments defining a space therebetween, and wherein the other leg of said at least two legs is aligned with said space.

11. A clip according to claim 1, wherein each of said at least two legs comprises a plurality of parallel leg segments defining spaces therebetween, and wherein a leg segment of one of said at least two legs is aligned with a space of the other of said at least two legs.

12. A clip according to claim 1, wherein at least one of said at least two legs comprises at least three parallel non-planar leg segments.

13. A clip according to claim 1, further comprising a tissue stop segment extending from one of said at least two legs.

14. A clip according to claim 13, wherein said at least two legs are deflectable to an open position wherein said legs are spaced from each other to receive tissue therebetween, wherein said head portion has a gap defined between said at least two legs in said open position, and wherein said tissue stop segment extends across said gap to prevent entry of tissue into said head portion.

15. A clip according to claim 1, wherein at least said head portion is made of a material having elasticity sufficient to allow said at least two legs to be spread to said open position for receiving tissue therebetween, and to return toward said closed position wherein said at least two legs are substantially adjacent to each other.

16. A clip according to claim 1, wherein said clip is formed from a single wire having a first wire end and a second wire end, said wire being formed into a loop defining said head portion, and extending to define a first leg of said at least two legs which terminates in said first wire end, and extending from said loop to define a second leg of said at least two legs terminating in said second wire end.

17. A clip according to claim 16, wherein said wire of said second leg forms two parallel leg segments connected at a leg end spaced from said loop and said second leg terminates with said second wire end substantially adjacent to said loop.

18. A clip according to claim 17, wherein said second leg further includes a tissue stop segment extending substantially perpendicular from one of said two parallel leg segments from a position substantially adjacent to said loop and in a direction toward said first leg.

19. A clip according to claim 18, wherein said wire at said first leg forms two parallel leg segments connected at a leg end spaced from said loop and terminating in said first wire end substantially adjacent to said loop.

20. A clip according to claim 1, wherein said at least two legs have contacting portions, and said contacting portions have a textured surface to enhance gripping of tissue.

21. A clip according to claim 1, wherein said legs are resiliently biased toward an arcuate shape defining concave curved sides in said open position which are arranged facing each other.

22. A clip according to claim 21, wherein said legs in said closed position are deflected from said arcuate shape toward a straight shape.

23. A clip according to claim 1, wherein said head portion is a resilient wire formed into a loop having a plurality of turns.

24. A ligating clip, comprising:

a substantially planar head portion;

at least two legs each extending away from said head portion, said legs being positionable between a closed position for clipping tissue and an open position wherein said legs are spaced from each other to receive tissue therebetween, and wherein said head portion has a gap defined between said at least two legs in said open position; and a tissue stop member extending from one of said at least two legs across said gap to prevent entry of tissue into said head portion, wherein said one of said at least two legs and said tissue stop member are formed from a single piece of material.

25. A clip according to claim 24, wherein said clip is formed from said single piece of material.

26. A clip according to claim 25, wherein said single piece of material is a wire having two ends, and wherein said tissue stop member terminates in one of said two ends.

* * * * *